United States Patent
McDonnell et al.

(10) Patent No.: US 6,905,477 B2
(45) Date of Patent: Jun. 14, 2005

(54) CATHETER WITH IMPROVED TRANSITION SECTION

(75) Inventors: Paula McDonnell, Galway (IE); Mark Casley, Galway (IE); Declan Costello, Galway (IE); William Hawkins, Wayzata, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 205 days.

(21) Appl. No.: 10/251,477

(22) Filed: Sep. 20, 2002

(65) Prior Publication Data

US 2004/0059291 A1 Mar. 25, 2004

(51) Int. Cl.⁷ .............................................. A61M 31/00
(52) U.S. Cl. .................................. 604/103.04; 604/528
(58) Field of Search ................................. 604/509–510, 604/95.03, 95.04, 96.01–97.02, 102.01–102.03, 103–103.04, 104, 164.1, 523–525, 915, 917, 919, 101.01–101.05; 606/191–199; 623/1.1, 1.11, 1.12, 1.15

(56) References Cited

U.S. PATENT DOCUMENTS

| 4,988,356 A | 1/1991 | Crittenden et al. |
| 5,334,187 A | 8/1994 | Fischell et al. |
| 5,718,680 A | 2/1998 | Kraus et al. |
| 2003/0191491 A1 * | 10/2003 | Duane et al. ............... 606/194 |

* cited by examiner

*Primary Examiner*—Nicholas D. Lucchesi
*Assistant Examiner*—Michael M. Thompson

(57) ABSTRACT

A catheter and guide wire exchange system including a catheter that has a guide wire lumen with a guide way extending along a length of the proximal shaft. A guide member is slidably disposed about the proximal shaft for directing a guide wire into or out of the guide way and the guide wire lumen. A transition section joins the bilumen proximal shaft to a coaxial distal shaft.

10 Claims, 19 Drawing Sheets

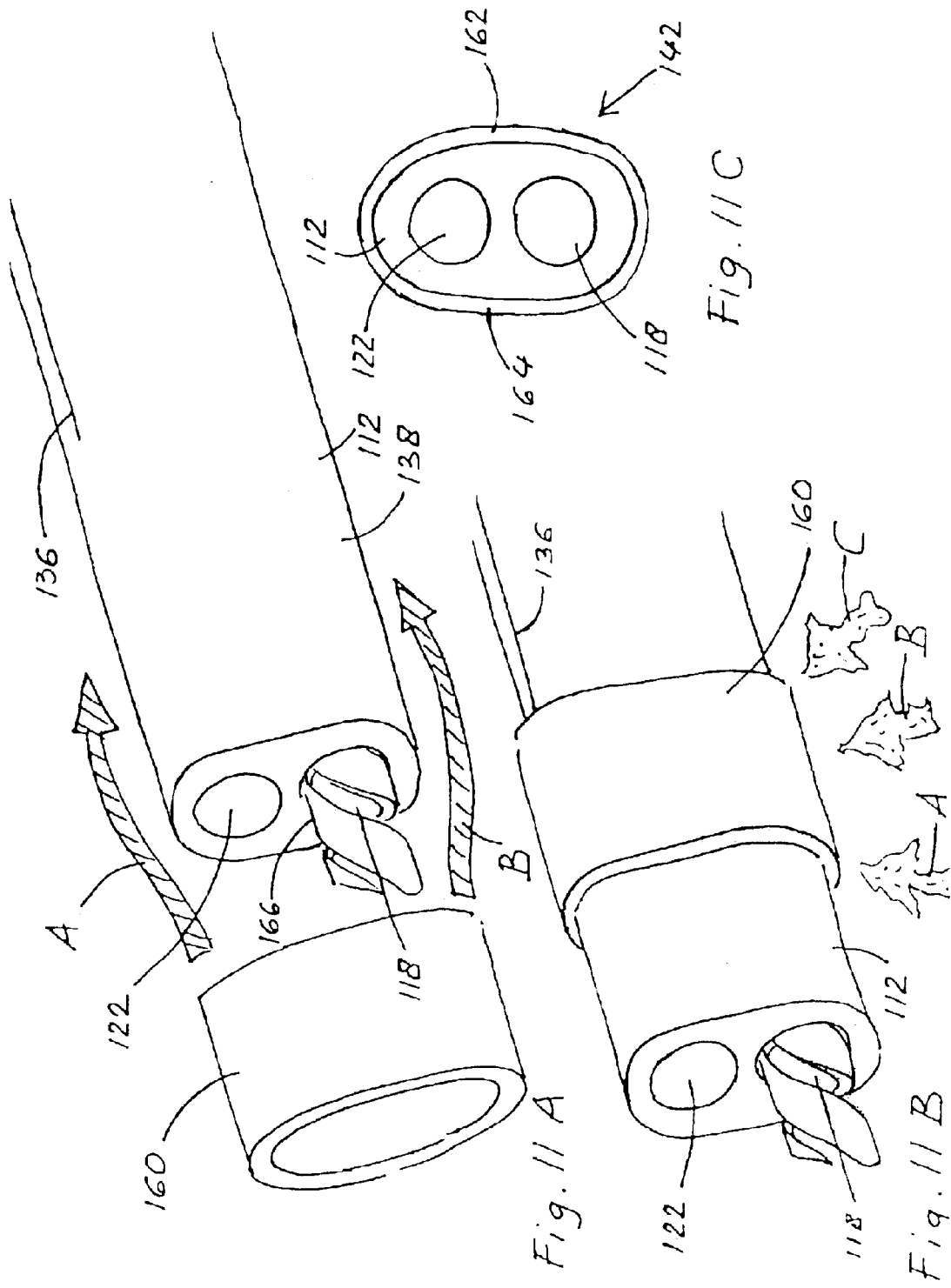

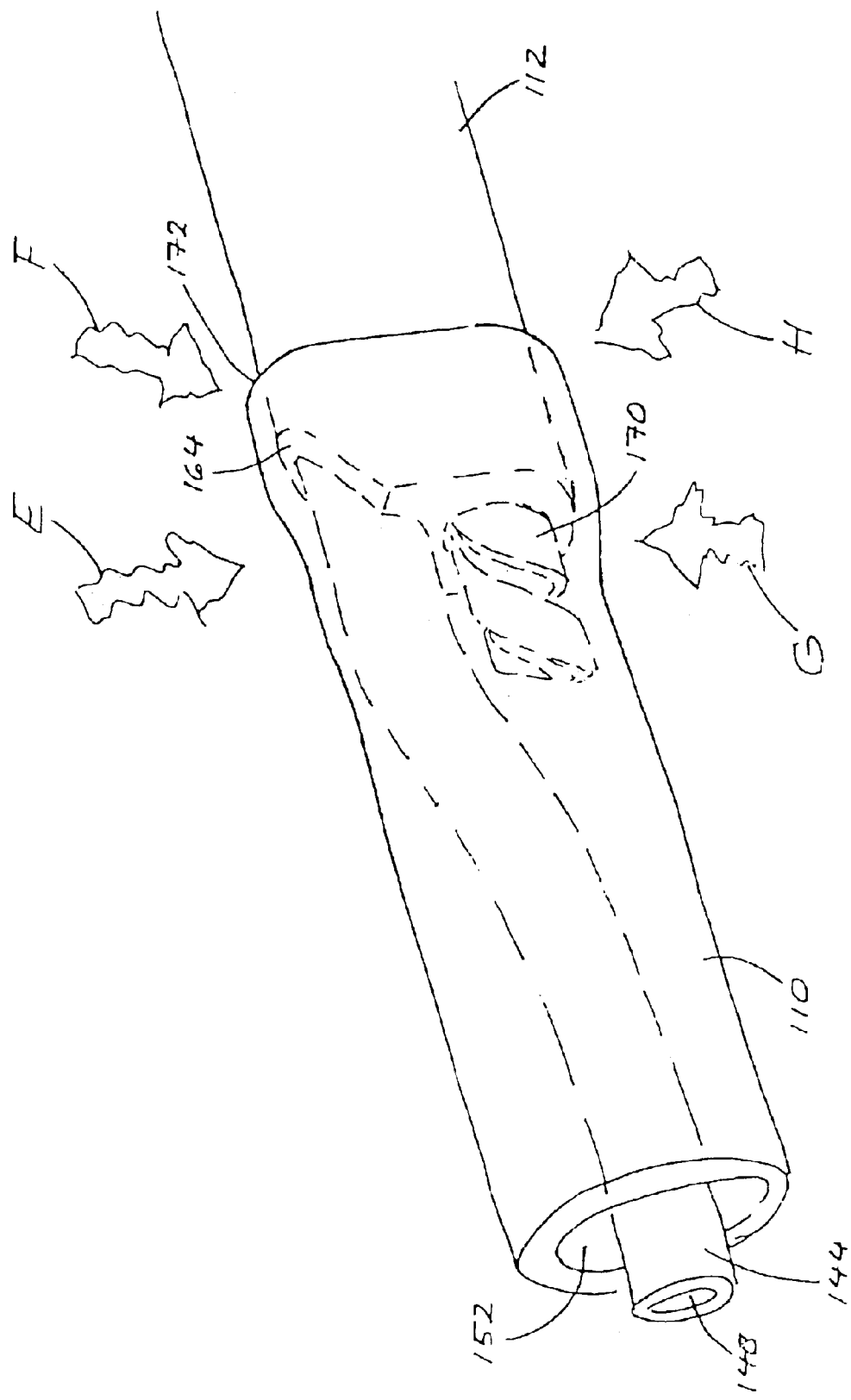

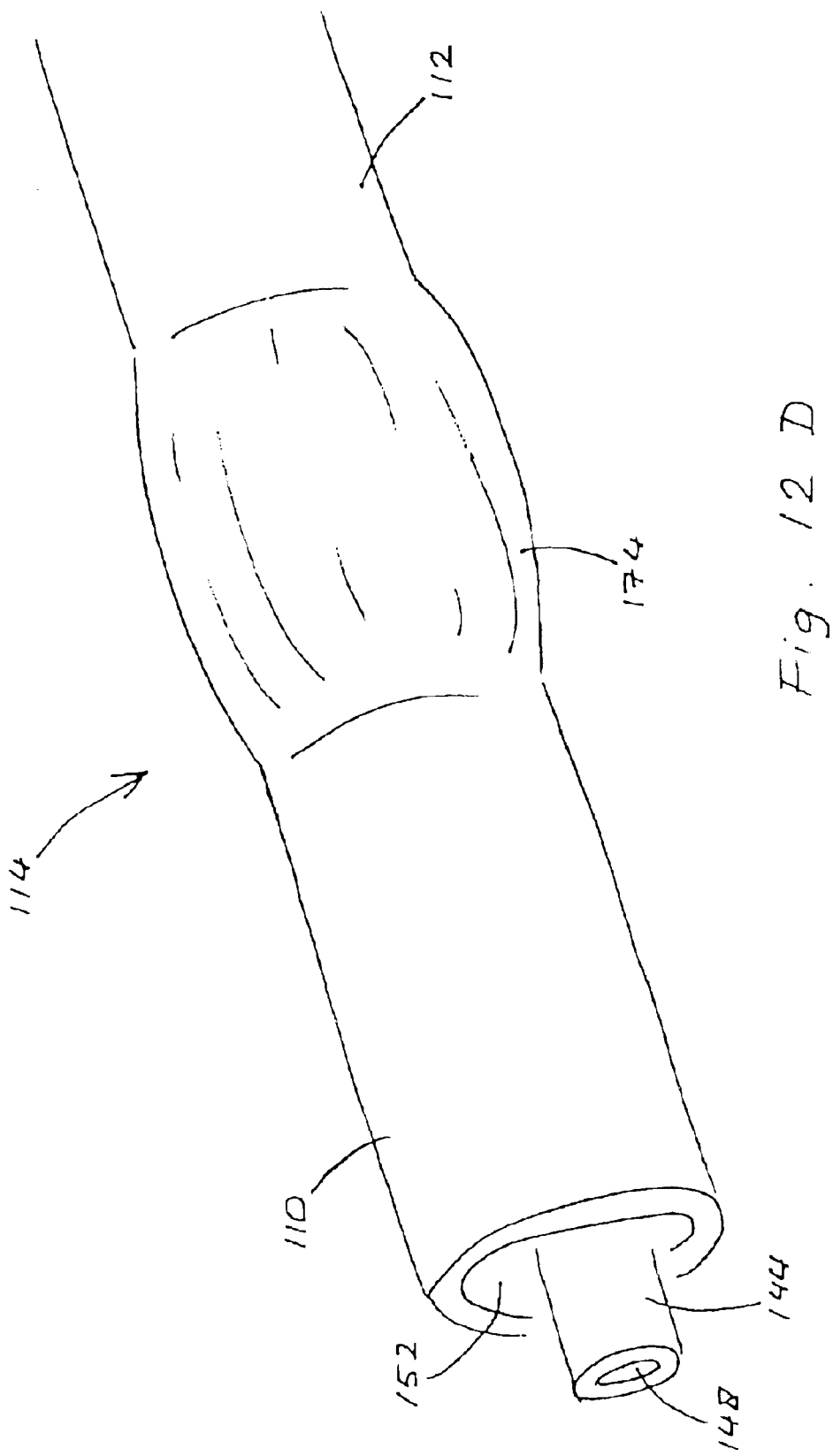

CATHETER WITH IMPROVED TRANSITION SECTION

FIELD OF THE INVENTION

The present invention relates to catheters used with guide wires in the cardiovascular system and, in particular, to a system for facilitating exchange of such catheters and guide wires, and for transporting such catheters and guide wires to selected sites within a patient.

BACKGROUND OF THE INVENTION

Catheters are inserted to various locations within a patient for a wide variety of purposes and medical procedures. For example only, one type of catheter is used in percutaneous catheter intervention (PCI) for the treatment of a vascular constriction termed a stenosis. In this instance, the catheter has a distally mounted balloon that can be placed, in a deflated condition, within the stenosis, and then inflated to dilate the narrowed lumen of the blood vessel. Such balloon dilation therapy is generally named percutaneous transluminal angioplasty (PTA). The designation PTCA, for percutaneous transluminal coronary angioplasty, is used when the treatment is more specifically employed in vessels of the heart. PTCA is used to open coronary arteries that have been occluded by a build-up of cholesterol, fats or atherosclerotic plaque. The balloon at the distal end of the catheter is inflated, causing the site of the stenosis to widen.

The dilation of the occlusion, however, can form flaps, fissures and dissections, which may result in reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. A stent is typically a cylindrically shaped device formed from wire(s) or a tube and is intended to act as a permanent prosthesis. Stents may include therapeutic coatings or deliver therapeutic drugs to further treat the vessel and prevent reclosure of the vessel. A stent is deployed in a body lumen from a radially compressed configuration into a radially expanded configuration that allows it to contact and support a body lumen. A stent can be implanted during an angioplasty procedure by using a balloon catheter bearing a compressed stent that has been loaded onto the balloon. The stent radially expands as the balloon is inflated, forcing the stent into contact with the body lumen, thereby forming a supporting relationship with the lumen walls. Alternatively, self-expanding stents may be deployed with a sheath-based delivery catheter. Deployment is effected after the stent has been introduced percutaneously, transported transluminally and positioned at a desired location by the delivery catheter. In addition to angioplasty and stenting procedures, other therapeutic procedures require use of a delivery catheter, such as drug delivery, filters, occlusion devices, diagnostic devices and radiation treatment.

Typically, the placement of such therapeutic delivery catheters involves the use of a guide wire, which may be inserted into the patient's vasculature through the skin, and advanced to the location of the treatment site. The delivery catheter, which has a lumen adapted to receive the guide wire, then is advanced over the guide wire. Alternatively, the guide wire and the delivery catheter may be advanced together, with the guide wire protruding from the distal end of the delivery catheter. In either case, the guide wire serves to guide the delivery catheter to the location to be treated.

To treat small diameter vessels remote from the entry point into the patient, a guide catheter is used to span the distance. For example, in PTCA or stent delivery, a guide catheter 10 is typically inserted into a large artery 12 near the patient's groin, and then advanced toward the heart 14 to the entry opening, or ostium, of the diseased coronary artery as illustrated in FIG. 1A. The guide catheter 10 provides a tubular conduit through which catheters and guide wires, designated generally as 16, can be passed from outside the patient to the vessel being treated.

There are three general types of catheters: "over-the-wire" (OTW) catheters, "rapid exchange" (RX) or single operator catheters and "fixed wire" (FW) or "a balloon on a wire" catheters. An over-the-wire catheter comprises a guide wire lumen that extends the entire length of the catheter. The guide wire is disposed entirely within the catheter guide wire lumen except for the distal and proximal portions of the guide wire, which extend beyond the distal and proximal ends of the catheter respectively. An OTW catheter typically has a "co-axial" catheter construction, as shown in FIGS. 2A and 3A, wherein two hollow tubes are nested together such that the lumen 22 of the inner tube can slidably receive guide wires, such as guide wire 24, and the annular luminal space 26 formed between the inner and outer tubes is used for inflation/deflation, fluid. An alternative "multilumen" OTW catheter construction has an elongate shaft made from a single extruded tube 18 having two lumens 22' and 26' formed side-by-side, as shown in FIGS. 2B and 3B. OTW catheters that contain both multilumen segments and coaxial segments are also known.

Over-the-wire catheters have many advantages traceable to the presence of a full-length guide wire lumen such as good stiffness and pushability for readily advancing the catheter through the tortuous vasculature and across tight stenoses. The full-length guide wire lumen permits removal and replacement of a guide wire in an indwelling catheter, as may be required to alter the shape of the guide wire tip. It is also sometimes desirable to exchange one guide wire for another guide wire having a different stiffness. For example, a relatively soft, or flexible guide wire may prove to be suitable for guiding a PTCA catheter through a particularly tortuous anatomy, whereas following up with a stent-delivery catheter through the same vasculature region may require a guide wire that is relatively stiffer. The full-length guide wire lumen is also available for transporting radio-contrast dye to the stenosed artery, for making pressure measurements, for infusing drugs and for other therapies.

Over-the-wire catheters do suffer some shortcomings, however. For example, it often becomes necessary, in the performance of a PCI, to exchange one indwelling catheter for another catheter. In order to maintain a guide wire in position while withdrawing the catheter, the guide wire must be gripped at its proximal end to prevent it from being pulled out of the blood vessel with the catheter. For example, a PTCA catheter, which may typically be on the order of 135 centimeters long, is longer than the proximal portion of the standard guide wire that protrudes out of patient. Therefore, exchanging an over-the-wire PTCA catheter requires an exchange guide wire of about 300 centimeters long, whereas a standard guide wire is about 165 centimeters long.

In one type of over-the-wire catheter exchange, the standard length guide wire first is removed from the lumen of the indwelling catheter. Then, a longer exchange guide wire is passed through the catheter to replace the original wire. Next, while holding the exchange guide wire by its proximal end to control its position in the patient, the catheter is withdrawn proximally from the blood vessel over the exchange guide wire. After the first catheter has been removed, the next OTW catheter is threaded onto the proximal end of the exchange guide wire and is advanced along the exchange guide wire, through the guiding catheter, and into the patient's blood vessels until the distal end of the catheter is at the desired location. The exchange guide wire may be left in place or it may be exchanged for a shorter, conventional-length guide wire. In an alternative type of catheter exchange procedure, the length of the initial guide wire may be extended by way of a guide wire extension apparatus. Regardless of which exchange process is used, the very long exchange guide wire is awkward to handle, thus requiring at least two operators to perform the procedure.

Catheter designs have been developed in an attempt to eliminate the need for guide wire extensions or exchange guide wires. One such catheter design is the rapid exchange (RX) type catheter. Catheters of this type are formed so that the guide wire is located outside of the catheter except for a short guide wire lumen that extends within only a comparatively short distal segment of the catheter. The rapid exchange catheter's proximal exit port for the guide wire is typically located about 5 cm (2.0 in) to 100 cm (11.8 in) proximal to the catheter's distal end. In use, the guide wire is placed initially in the patient's vascular system. The distal segment of the RX catheter then is threaded onto the wire. The catheter can be advanced alongside the guide wire with its distal segment being attached to and guided along the guide wire. The RX catheter can be removed and exchanged for another RX catheter without the use of a very long exchange guide wire and without requiring withdrawal of the initially placed guide wire.

Although an RX catheter system may avoid the requirement for using a very long exchange wire, it presents several difficulties. First, without a full-length guide wire lumen, the proximal shaft of an RX catheter lacks an OTW catheter's coaxial interrelationship with the guide wire, which provides optimal transmission of force to push the distal end of the catheter through tight stenoses and/or tortuous blood vessels. FIGS. 2A and 3A illustrate guide catheter 10, a shaft segment of OTW catheter 18 extending there through, and guide wire 24 disposed within guide wire lumen 22 in the common construction of coaxial tubes. The nested tubes result in an inner guide wire lumen 22 and an annular inflation lumen 26 formed between the tubes. The coaxial interrelationship with guide wire 24 provides an optimal transmission of force along the catheter length. In FIGS. 2B and 3B, inflation lumen 26' extends parallel to guide wire lumen 22' in a side-by-side arrangement. Although guide wire lumen 22' and guide wire 24' are located off-center in catheter 18', guide wire 24' is confined within catheter 18' throughout its length. Even if catheter 18' begins to buckle slightly when the distal tip of the catheter is being forced through a tight stenosis, there is very little misalignment with guide wire 24', such that most of the push force is transmitted to the distal tip. Therefore, despite their disadvantages during catheter exchange procedures, OTW catheters remain popular in the United States, due in part to the coaxial alignment between the catheter shaft and the guide wire, and the resulting excellent pushability of the device.

While improvements to RX catheters have incorporated stiff, metal proximal shafts and axial overlap between the shaft and the guide wire lumen to overcome the deficiencies discussed above, such RX catheters still are not optimal. FIGS. 4 and 5 depict prior art RX catheter 30 incorporating such a reinforced shaft 32, disposed over guide wire 34 within guide catheter 36. However, even with continuous column support of reinforced shaft 32, the non-aligned or offset arrangement of guide wire 34 and shaft 32 of catheter 30 can cause shaft buckling within the guiding catheter, as illustrated generally at 38 in FIG. 4, especially when the distal tip of the catheter is being forced through a tight stenosis. Such a non-coaxial misalignment causes displacement of push forces and an associated resistance to catheter advancement, especially in the region of proximal guide wire port 40.

A second difficulty associated with RX catheters is that it is not possible to exchange guide wires in an indwelling RX catheter, as can be done advantageously with OTW catheters. A guide wire can be withdrawn, sometimes unintentionally, from the proximal guide wire port, thus derailing an indwelling RX catheter. However, neither the first guide wire, nor a replacement guide wire, can be directed back into the catheter's proximal guide wire port, which is hidden remotely in the guiding catheter within the patient. FIG. 6 illustrates the problem of blindly steering the tip of guide wire 42 within guiding catheter 44 in an attempt to find and engage proximal guide wire port 46 of RX catheter 48.

A third difficulty associated with RX catheters is that, if the guide wire lumen is so short that the proximal guide wire port exits from the distal end of the guiding catheter, then the guide wire will be exposed. Such an RX device presents a risk of what is called the "cheese cutter effect," which is damage to the delicate inner surface of a curved artery from straightening tension applied to the exposed guide wire during push-pull maneuvers to advance the catheter. The short-lumen RX device also presents an increased risk of guide wire entanglement in those procedures where multiple guide wires are used, because the guide wires are exposed within the blood vessel. Furthermore, the exposed, unprotected portion of the guide wire can become kinked or tangled within the patient's vessel, adding complications to the procedure.

A fourth difficulty associated with RX catheters is encountered at the proximal end of the catheter system. There, the RX catheter and the guide wire extend from the guiding catheter side-by-side, making it awkward to seal the system against blood loss during manipulation of the components. The sealing, or "anti-backbleed" function is typically accomplished with a "Tuohy-Borst" fitting that has a manually adjustable gasket with a round center hole that does not conform well to the side-by-side arrangement of a catheter shaft and guide wire. A final difficulty associated with RX catheters is that the lack of a full-length guide wire lumen deprives the clinician of an additional lumen that may be used for other purposes, such as pressure measurement, injection of contrast dye distal to the stenosis, or infusing a drug.

An over-the-wire catheter designed to eliminate the need for guide wire extensions or exchange wires is disclosed in U.S. Pat. No. 4,988,356 (Crittenden et al.). This over-the-wire/short wire (OTW/SW) catheter includes a catheter shaft having a cut that extends longitudinally between the proximal end and the distal end of the catheter and that extends radially from the catheter shaft outer surface to the guide wire lumen. A guide member slidably coupled to the catheter shaft functions to open the cut such that the guide wire may extend transversely into or out of the cut at any location along its length. By moving the guide member, the effective over-the-wire length of the OTW/SW catheter is adjustable.

When using the OTW/SW catheter, the guide wire is maneuvered through the patient's vascular system such that the distal end of the guide wire is positioned across the treatment site. With the guide member positioned near the distal end of the catheter, the proximal end of the guide wire is threaded into the guide wire lumen opening at the distal end of the catheter and through the guide member such that the proximal end of the guide wire protrudes out the proximal end of the guide member. By securing the guide member and the proximal end of the guide wire in a fixed position, the catheter may then be transported over the guide wire by advancing the catheter toward the guide member. In doing so, the catheter advances through the guide member such that the guide wire lumen envelops the guide wire as the catheter is advanced into the patient's vasculature. In a PTCA embodiment, the OTW/SW catheter may be advanced over the guide wire in this manner until the distal end of the catheter having the dilatation balloon is positioned within the stenosis and essentially the entire length of the guide wire is encompassed within the guide wire lumen.

Furthermore, the indwelling OTW/SW catheter may be exchanged with another catheter by reversing the operation described above. To this end, the indwelling catheter may be removed by withdrawing the proximal end of the catheter from the patient while holding the proximal end of the guide wire and the guide member in a fixed position. When the catheter has been withdrawn to the point where the distal end of the cut has reached the guide member, the distal portion of the catheter over the guide wire is of a sufficiently short length that the catheter may be drawn over the proximal end of the guide wire without releasing control of the guide wire or disturbing its position within the patient. After the catheter has been removed, another OTW/SW catheter may be threaded onto the guide wire and advanced over the guide wire in the same manner described above with regard to the OTW/SW catheter. The OTW/SW catheter not only permits catheter exchange without the use of the very long exchange guide wire and without requiring withdrawal of the initially placed guide wire, but it also overcomes many of the other difficulties discussed in association with RX catheters.

Despite these advantages, original OTW/SW catheters in accordance with the '356 patent had difficulties related to movement of the guide wire through the guide member. As disclosed in the '356 patent, the use of a hypodermic tubing member to direct a guide wire into and out of the guide wire lumen was found to be effective while the guide wire was stationary within the guide member, and while the catheter was moved therethrough. However, if the guide wire were to be withdrawn through the guide member, the hypodermic tubing member would often scrape pieces of a lubricious coating from the guide wire. The resulting shavings, designated generally as 50 in FIG. 7, would become jammed in the annular space between the guide wire 52 and the hypodermic tubing member 54, preventing further movement of the guide wire.

In a more significant problem with the original OTW/SW catheter, it could fail to adequately contain the guide wire within the guide wire lumen during normal operation. In particular, as the catheter was advanced over the guide wire, the catheter could bend or buckle such that the guide wire could protrude from the catheter shaft. If the guide wire protruded from the catheter shaft, it could subsequently become pinched, and the distal end of the guide wire could be pulled out of or pushed beyond the treatment site, thus complicating the procedure and requiring repositioning within the patient's vasculature. Bending or buckling of a OTW/SW catheter could also occur proximal to the guide member, where the guide wire is absent from the guide wire lumen. Furthermore, the transition between the proximal shaft containing the longitudinal cut and the distal part of the catheter is also a potential kink location. It is among the general objects of the invention to provide an improved device that overcomes the foregoing difficulties.

SUMMARY OF THE INVENTION

The present invention is a catheter and guide wire exchange system comprising an elongate flexible catheter having proximal and distal ends and first and second lumens extending there through, the first lumen being open at the shaft distal end and being sized and shaped to slidably receive a guide wire. The second lumen is an inflation lumen. The catheter has a bilumen proximal shaft and a coaxial distal shaft. The distal and proximal shafts are coupled through a transition section. At the transition section, an outer tubular portion of distal shaft overlaps the outer surface of the proximal shaft distal end. Proximal end of distal shaft inner tubular member is positioned within the first lumen of the proximal shaft. The shafts are then fused forming the transition section.

A guide member is mounted on catheter proximal shaft and is received in a guide way formed from a longitudinal cut in catheter proximal shaft to enable transverse access to the first lumen through the elongate flexible catheter. The guide way extends along a major portion of the length of the proximal shaft from a location adjacent the proximal end of the catheter to a location proximal to the proximal shaft distal end. A stop is located on the exterior of the proximal shaft distal end proximal to the transition section. The guide member cannot travel distally past the stop. An elongate stiffening member is disposed within the second lumen from the catheter proximal shaft to a location past the guide way distal end through the transition section and into the catheter distal shaft. A balloon is mounted about catheter distal segment, the balloon being in fluid communication with the second lumen. The guide member has a catheter passageway for slidably receiving the catheter shaft and a guide wire passageway for slidably receiving the guide wire. The guide member merges the guide wire and the catheter by guiding the guide wire transversely through the guide way in the catheter and into the first lumen. Conversely, the guide member can be used for separating the guide wire and catheter by guiding the guide wire transversely out of the first lumen through the guide way. The guide wire lumen may further include a ramp or recess to assist in aligning the guide wire with the guide wire passageway.

BRIEF DESCRIPTION OF THE DRAWINGS

These and other features, aspects and advantages of the present invention will become better understood with reference to the following description, appended claims, and accompanying drawings where:

FIG. 8A is a cross-section taken along line A—A of FIG. 8;

FIG. 8B is a cross-section taken along line B—B of FIG. 8A;

FIG. 8C is a cross-section taken along line C—C of FIG. 8A;

FIG. 8D is a cross-section taken along line D—D of FIG. 8A;

FIGS. 11A–11C are schematic illustrations of the construction of the stop member of the present invention;

DETAILED DESCRIPTION OF THE INVENTION

Figures 1A, 1B:
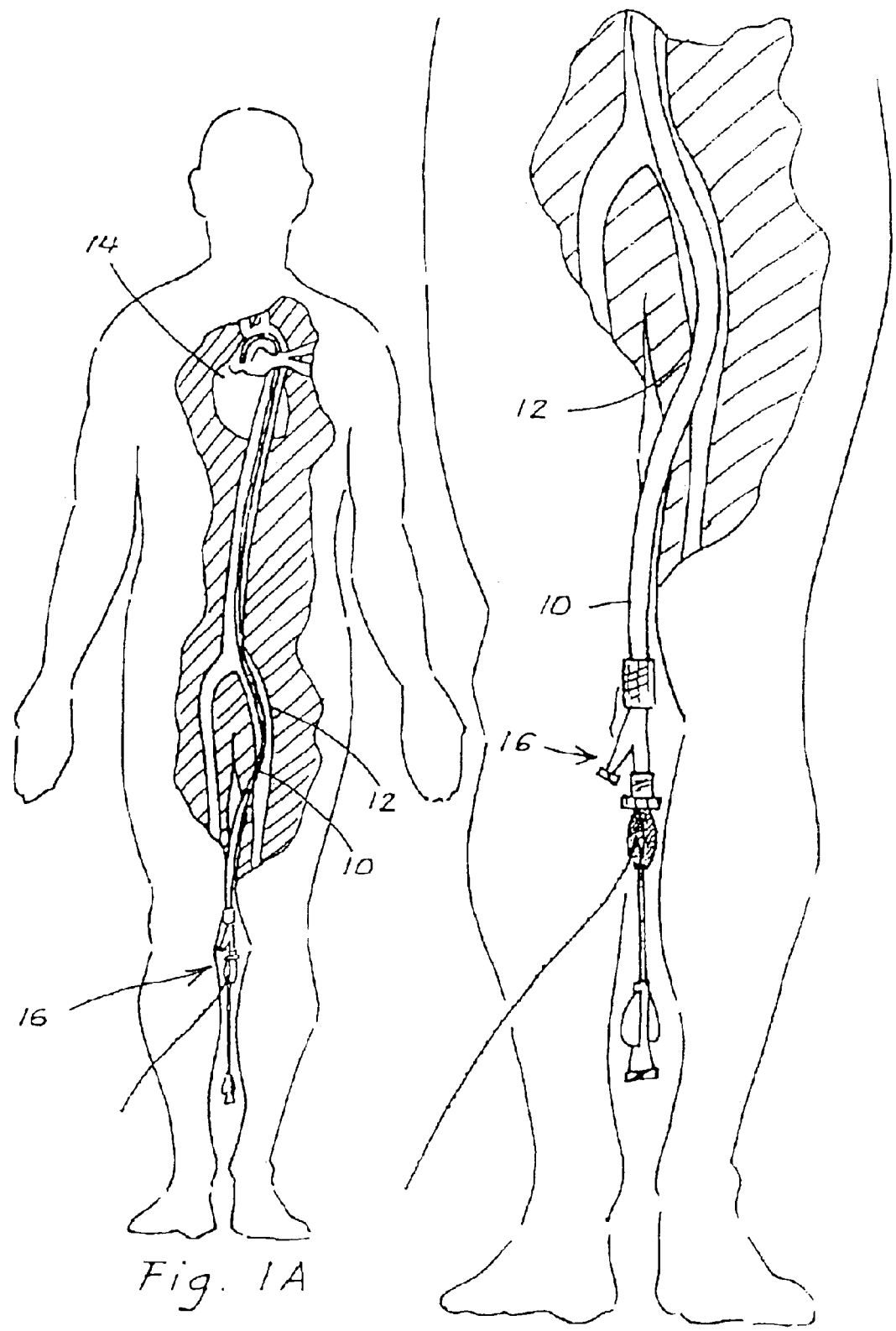
FIG. 1A is a diagrammatic illustration of a patient showing the manner in which a balloon catheter is advanced from the femoral artery through the aorta and into the patient's heart.
FIG. 1B is an enlarged portion of FIG. 1A showing the present invention positioned with the guide catheter and extending into the femoral artery.
Figure 2A:
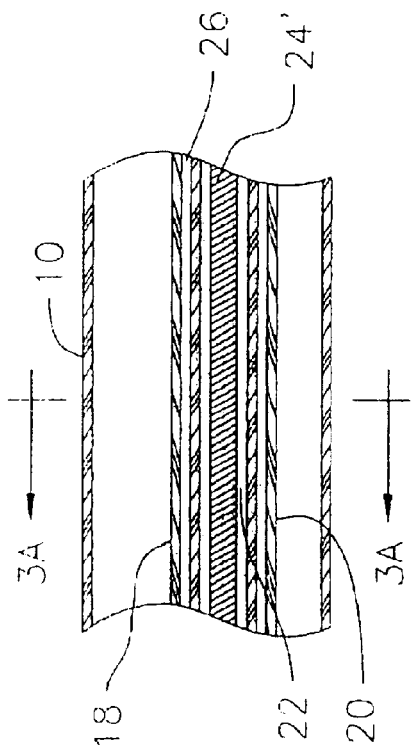
FIG. 2A is a longitudinal sectional illustration of a section of a prior art coaxial over-the-wire catheter and guide wire system.
Figure 2B:
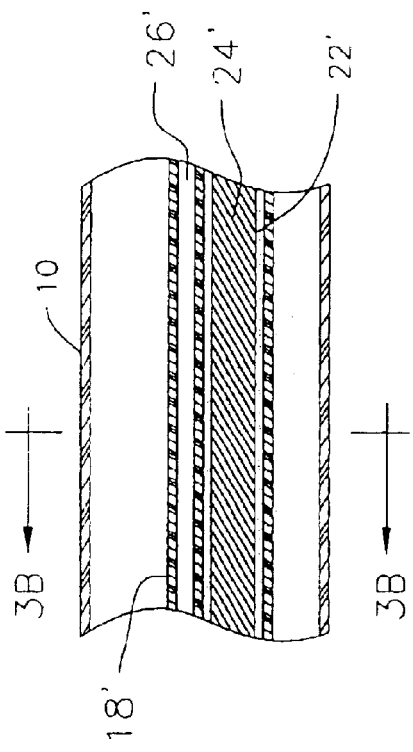
FIG. 2B is a longitudinal sectional illustration of a section of a prior art multilumen over-the-wire catheter and guide wire system.
Figure 3A:
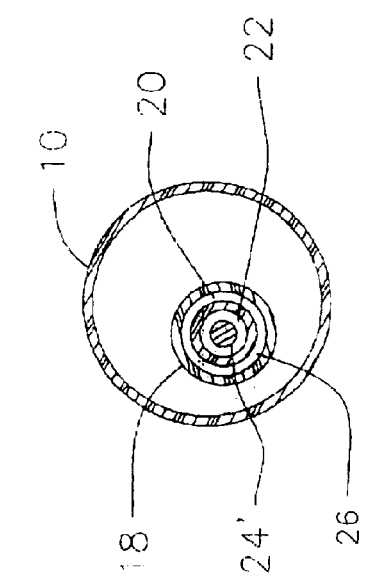
FIG. 3A is a transverse sectional illustration of a coaxial prior art over-the wire catheter and guide wire system, taken along the line 3A—3A of FIG. 2A.
Figure 3B:
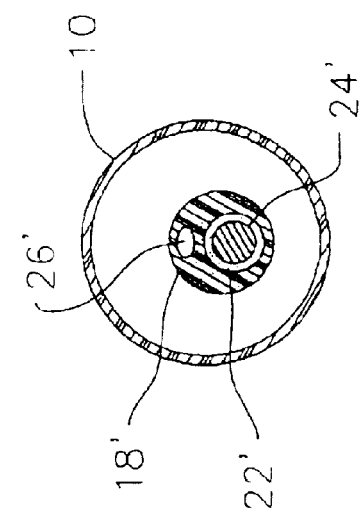
FIG. 3B is a transverse sectional illustration of a multi-lumen prior art over the-wire catheter and guide wire system, taken along the line 3B—3B of FIG. 2B.
Figure 4:
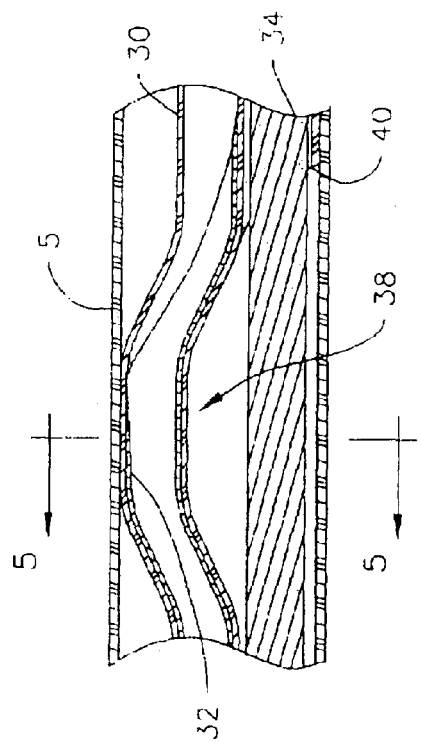
FIG. 4 is a longitudinal sectional illustration of a section of a prior art rapid exchange catheter and guide wire system.
Figure 5:
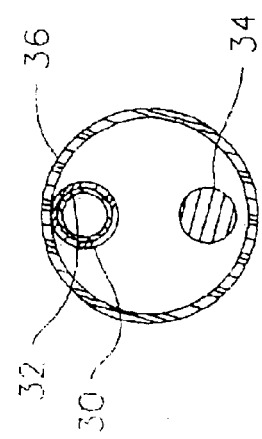
FIG. 5 is a transverse sectional illustration of a prior art rapid exchange catheter and guide wire system, taken along the line 5—5 of FIG. 4.
Figure 6:
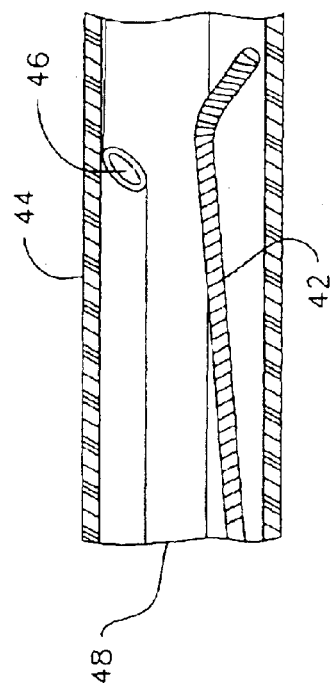
FIG. 6 is partial longitudinal sectional illustration of a section of a prior art rapid exchange catheter and guide wire system, shown within a guiding catheter.
Figure 7:
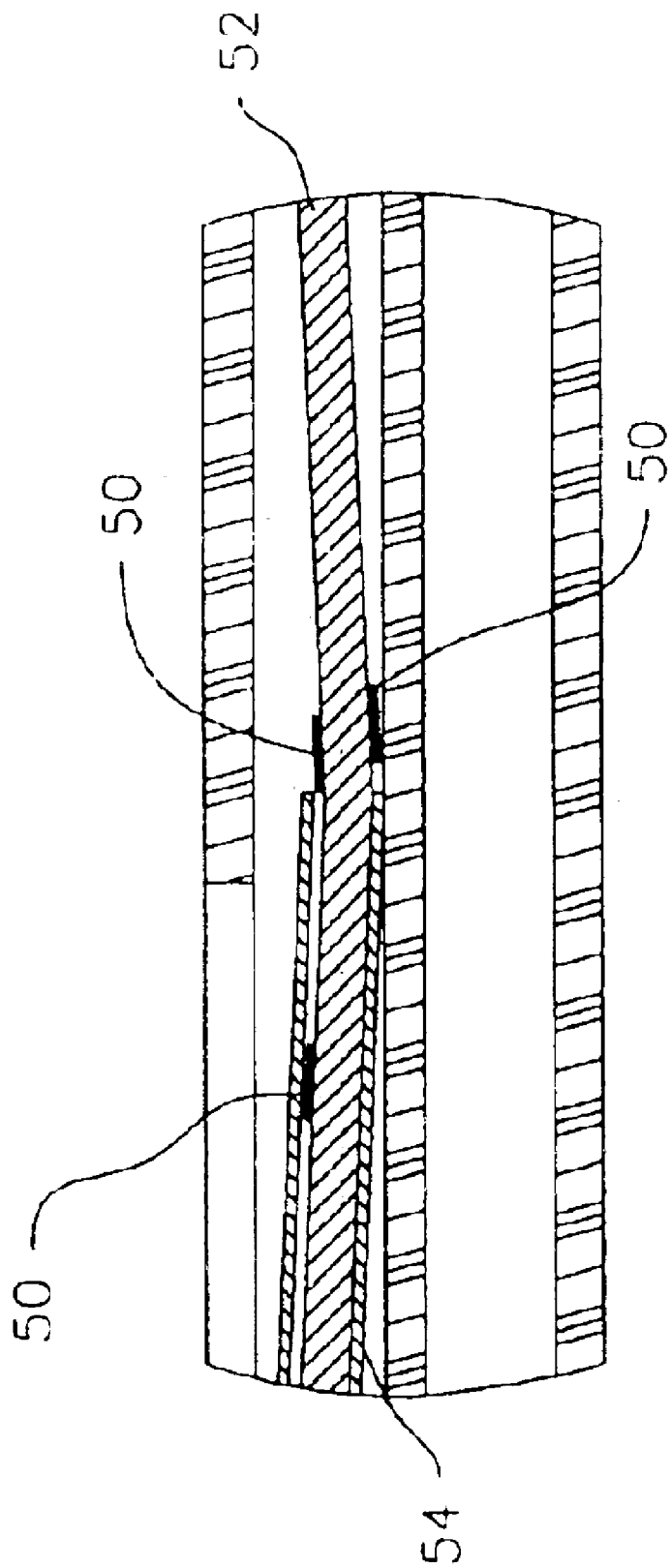
FIG. 7 is a partial longitudinal sectional illustration of a section of a prior art OTW/SW catheter and guide wire system.

As shown in FIG. 8A, the invention includes a catheter, indicated generally by the reference character 100, on which a guide member 102 is slidably mounted. Guide wire 104 is illustrated as extending through the guide member 102. Guide member 102 serves as a juncture in which the catheter 100 and guide wire 104 may be merged or separated so that the portion of guide wire 104 which extends proximally of guide member 102 (to the left as seen in FIG. 8A) is separated from catheter 100 and the portion of guide wire 104 which is located distally of guide member 102 (to the right as seen in FIG. 8A) is contained and housed within catheter 100 except for distal end 106 of guide wire 104 which may protrude distally out of distal end 108 of catheter 100.

Catheter 100 includes an elongate, flexible, cylindrical main body, which may be formed from an extruded plastic material such as, for example, polyethylene or polyethylene block amide (PEBA) copolymer. Catheter 100 has a distal shaft 110 and a proximal shaft 112 with a transition section designated 114. The embodiment shown in FIG. 8A, a catheter, such as for PTCA or stent delivery, having balloon 116 mounted around the catheter body near the distal end 108 of catheter 100. Balloon 116 may be inflated and deflated through inflation lumen 118 formed through the body of the catheter 100. Inflation lumen 118 extends from the proximal end of catheter 100, where it communicates with fitting 120 and extends the length of catheter 100, terminating in communication with the interior of balloon 116. Fitting 120 may be connected to a suitable source of pressurized fluid or a partial vacuum (not shown) to inflate or deflate balloon 116. Catheter 100 includes lumen 122 for receiving guide wire 104. Guide wire lumen 122 extends the full length of catheter 100, terminating at distal end 108 and proximal fitting 120.

In accordance with the invention, the body of proximal shaft catheter 100 is formed with longitudinal guide way 124 which, when catheter 100 is viewed in cross-section, as in FIG. 8A, may be considered as defining a pair of flaps 126 and 128 which normally close together at guide way 124 to define enclosed guide wire lumen 122. Guide wire lumen 122 may be circular in cross-section or may be non-circular; in either case, the cross-sectional dimensions of guide wire lumen 122 are greater than the cross-sectional dimension of guide wire 104 to permit relative longitudinal movement between guide wire 104 and catheter 100. Inflation lumen 118 encompasses elongate stiffening member 130, which causes the shaft of catheter 100 to have greater bending stiffness than guide wire 104. Stiffening member 130 extends at least through the length of catheter 100 that includes guide way 124, thus preventing the shaft from bending such that guide way 124 could buckle allowing guide wire 104 to protrude from the catheter shaft and it may extend into distal shaft 110. Guide way proximal end 132 may terminate at or near fitting 120. In the embodiment shown in FIG. 8A, guide way distal end 136 terminates short of proximal shaft distal end 138, thereby leaving distal section 140 of proximal shaft 112 in which guide wire lumen is defined by a continuous surrounding wall as shown in FIG. 8B. Stop 142 is located approximate guide way distal end 136. Stop 142 is a raised portion on the proximal shaft as seen in FIG. 8A. The raised portion may be annular or multiple areas spaced around the shaft circumference such as the two raised areas 162 and 164 spaced 180 degrees apart on the long axis of oval proximal shaft 112 as shown in FIG. 11C.

Figure 8:
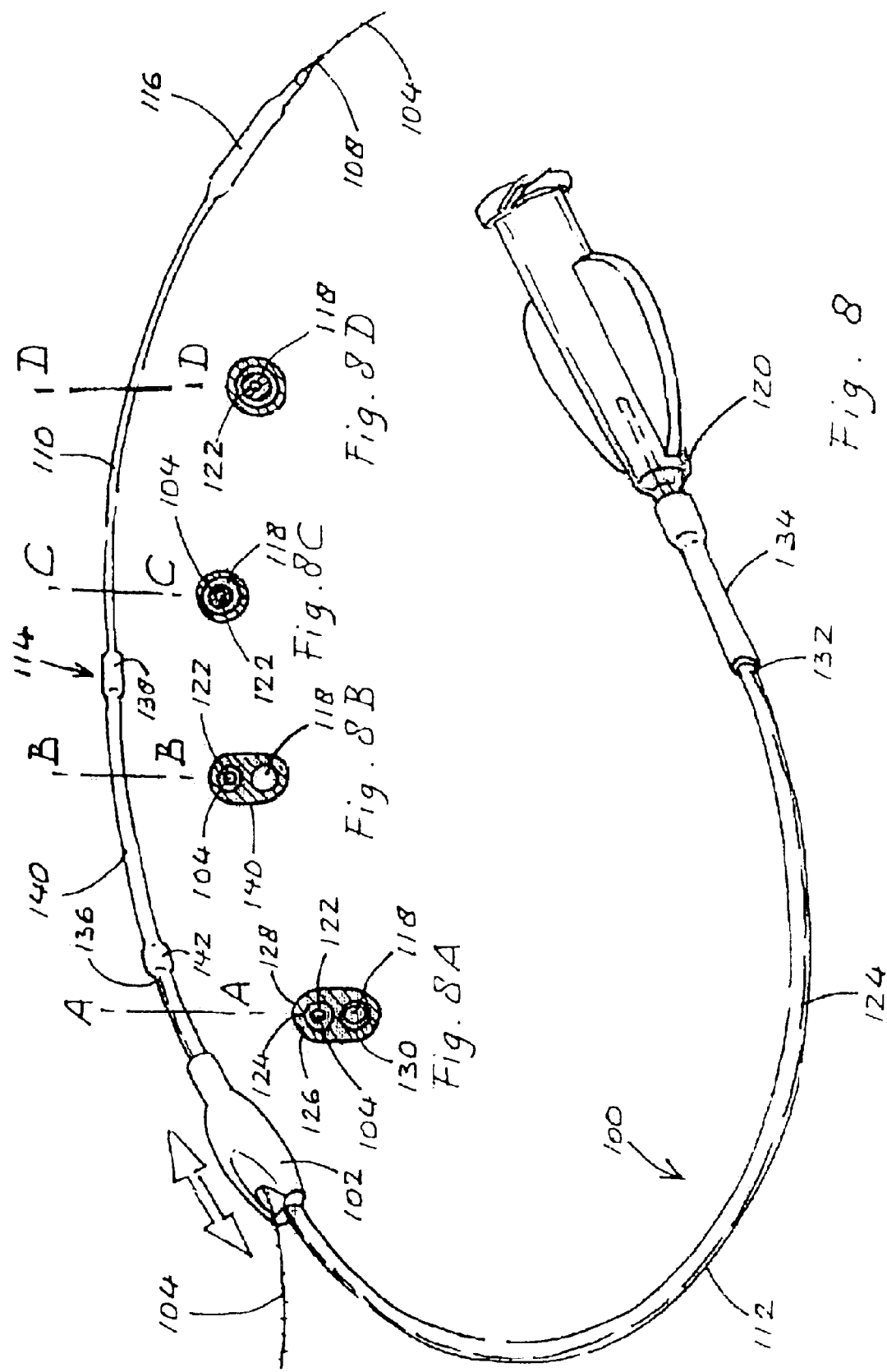
FIG. 8 is an illustration of the catheter and guide wire of the present invention in an assembled configuration.
Figure 9:
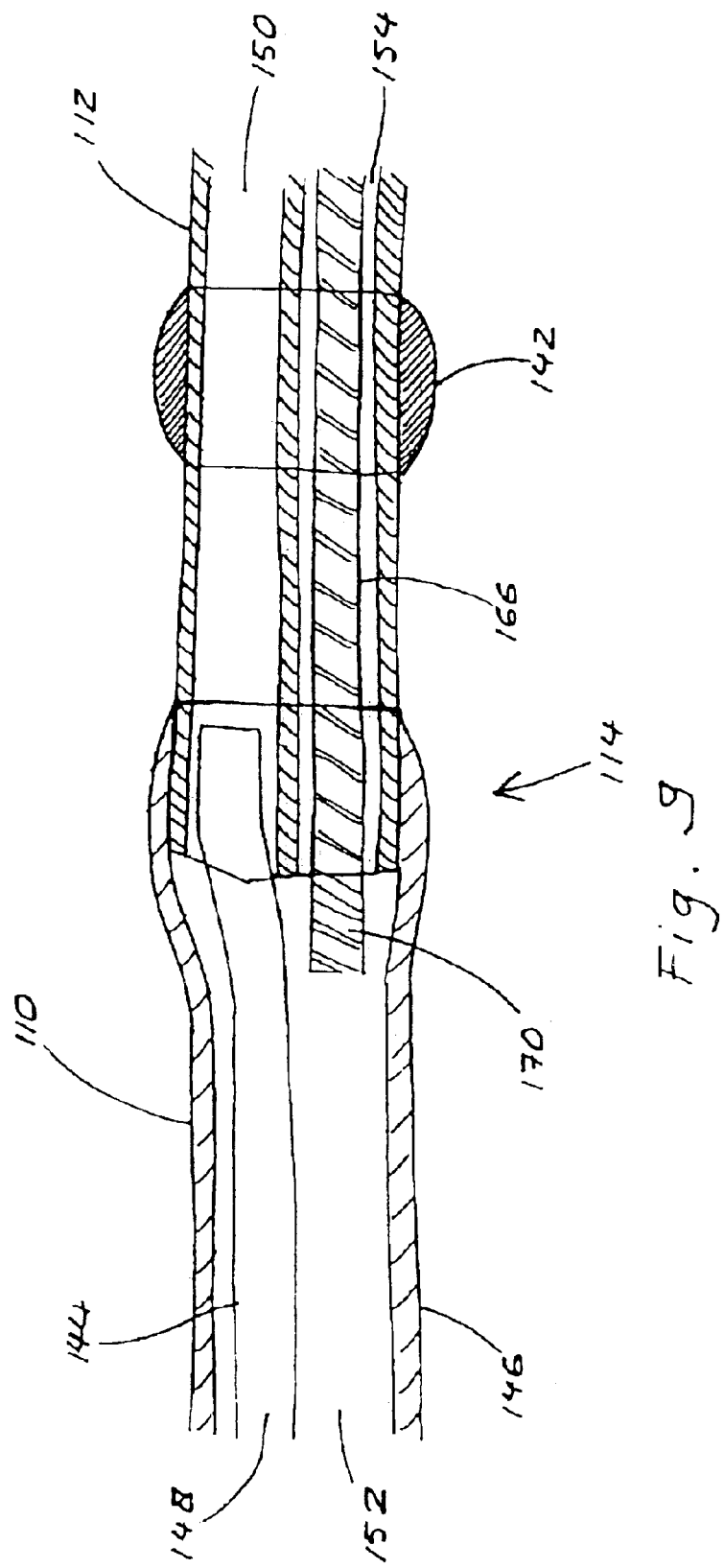
FIG. 9 is a transverse sectional illustration of the transition section of the present invention.
Figure 10A:
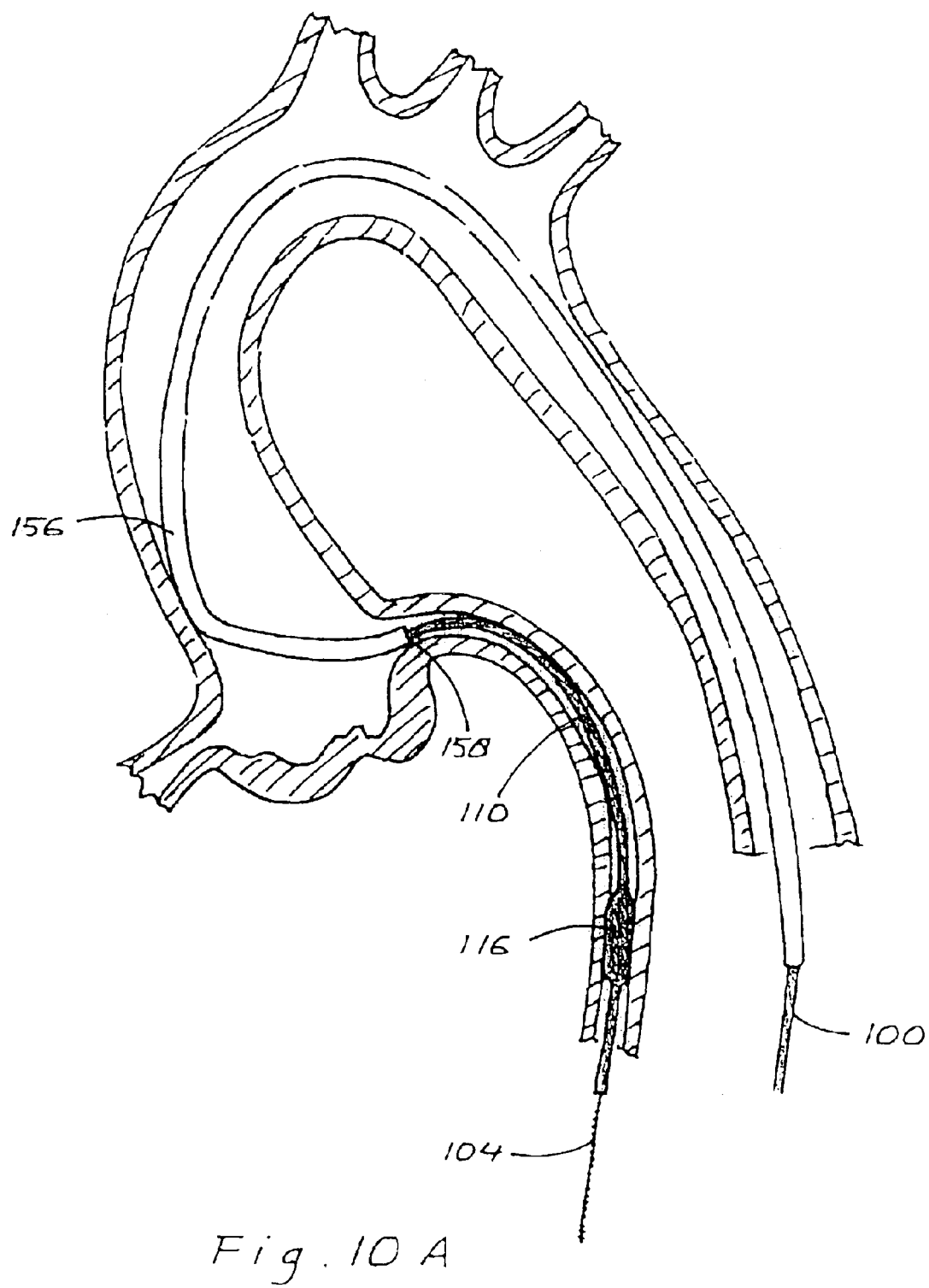
FIG. 10A is a large view of the present invention extending from the guide catheter at the ostium of the heart.
Figure 10:
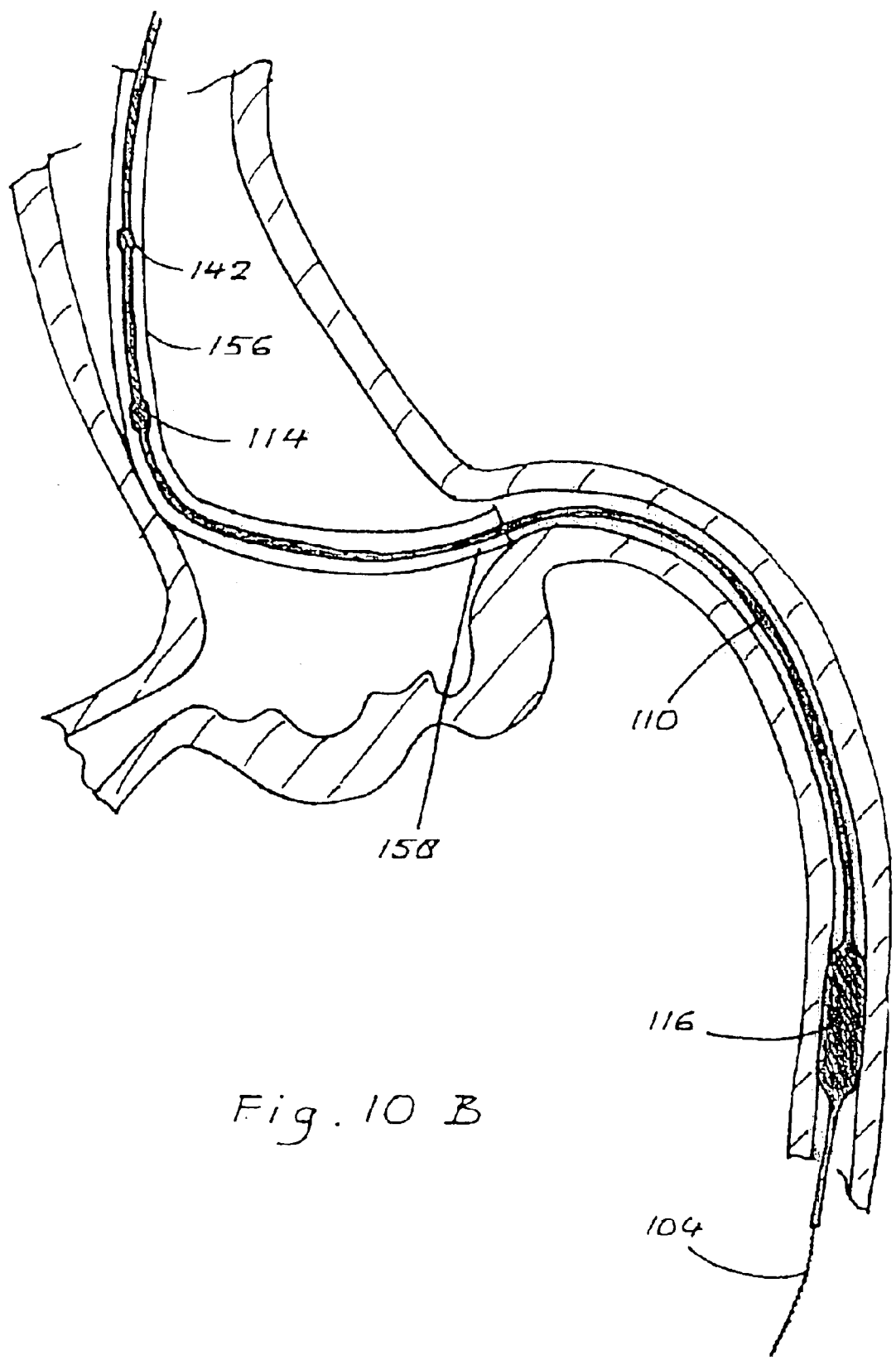
FIG. 10B is a cross-section of the guide catheter showing the present invention extending through the aortic arch of FIG. 1A.

Turning now to FIGS. 8B, 8C and 9, catheter 100 transforms from its proximal side-by-side lumen configuration to a distal coaxial configuration adjacent guide way distal end 136. Distal catheter shaft 110 preferably comprises a coaxial arrangement of two tubes 144 and 146, with inner tube lumen 148 communicating with proximal shaft guide wire lumen 150. Outer tube 146 encompasses the inner tube 144, forming an annular lumen 152 that extends proximal inflation lumen 154 to balloon 116. The length of catheter 100 is such that it can pass easily through the curved aortic arch as shown in FIGS. 10A and 10B. In these views, guide catheter 156 stops proximate the ostium of the heart and prior to the diseased coronary artery. Guide catheter 156 provides tubular conduit through which catheter 100 and guide wire 104 are passed through the patient from outside the patient to the vessel being treated, as illustrated in FIGS. 1A, 1B, 10A and 10B. As seen in FIG. 10B, transition section 114 is proximal of guide catheter opening 158 with distal shaft 110 extending out from guide catheter 156.

Prior to forming the transition section 114, stop 142 is formed on proximal shaft 112 as is seen in FIGS. 11A–C. Preferably, a tubular member 160, preferably made of polyethylene or other suitable material that may be fused with the proximal shaft, is placed over proximal shaft distal section 138, as shown by the arrows A and B, and positioned proximate guide way distal end 136 as seen in FIG. 11A. Heat, designated by the arrows A, B and C in FIG. 11B, is applied to fuse tubular member 160 to proximal shaft 112. As is well known to those of skill in the art, heat can be applied by any suitable heat source such as a hot air source or a laser source. By fusing the tubular member 160 onto generally proximal shaft 112, preferably two raised areas 162 and 164 spaced on opposing exterior surfaces of proximal shaft 112 are formed creating stop 142 as shown in FIG. 11C. Additionally, an annular raised surface may be formed about the exterior surface of proximal shaft 112 such as shown in FIG. 8. Stop 142 increases the outer diameter of proximal shaft 112 by an amount sufficient to prevent guide member 102 from moving distally past stop 142. Alternatively, stop 142 may be formed integrally with proximal shaft 112 when it is initially extruded or tubular member 160 may be secured with an adhesive as will be understood by those of skill in the art.

Figure 12A:
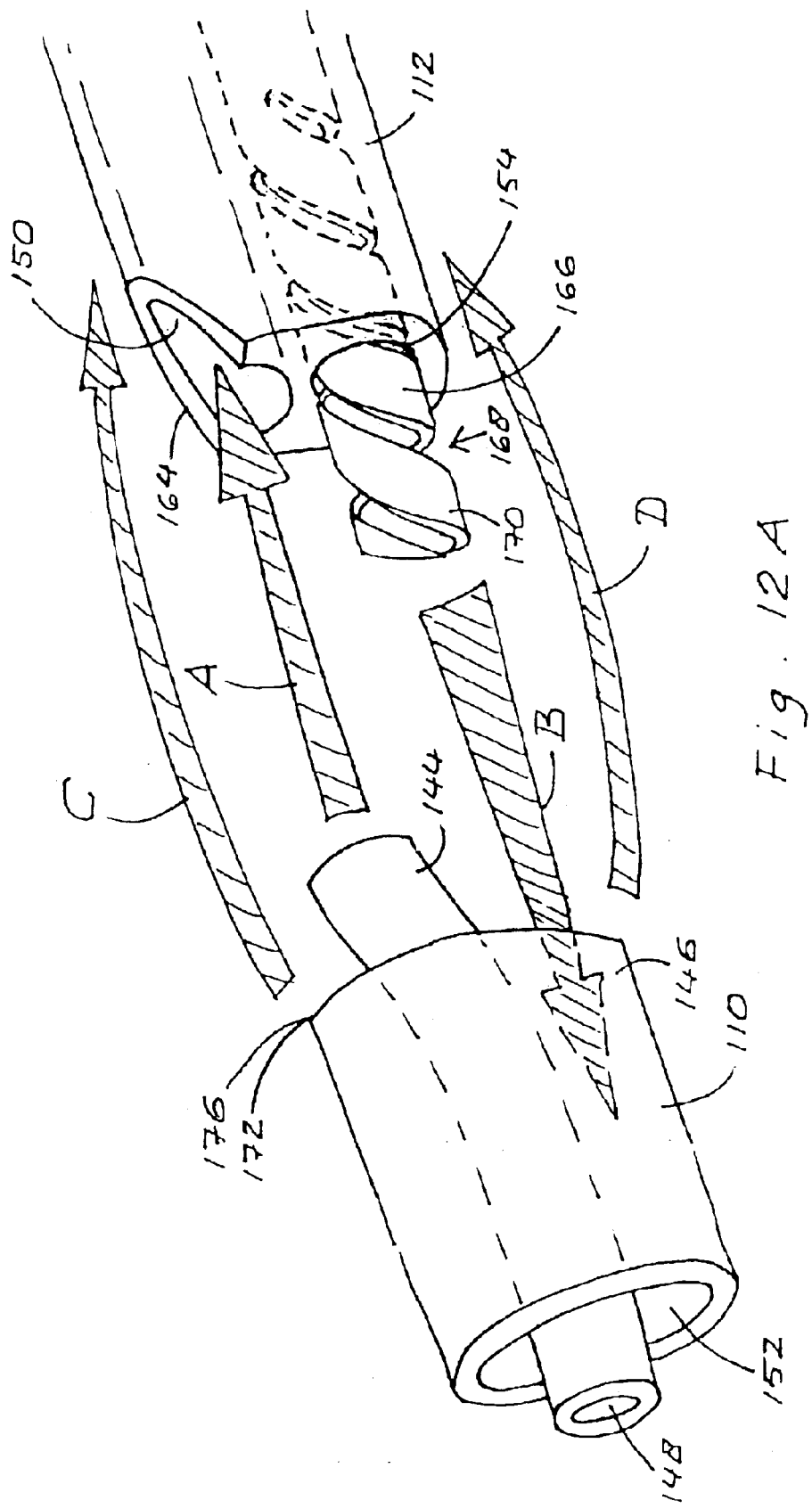
FIGS. 12A–12E are schematic illustrations of the construction of the transition section of the present invention.
Figure 12:
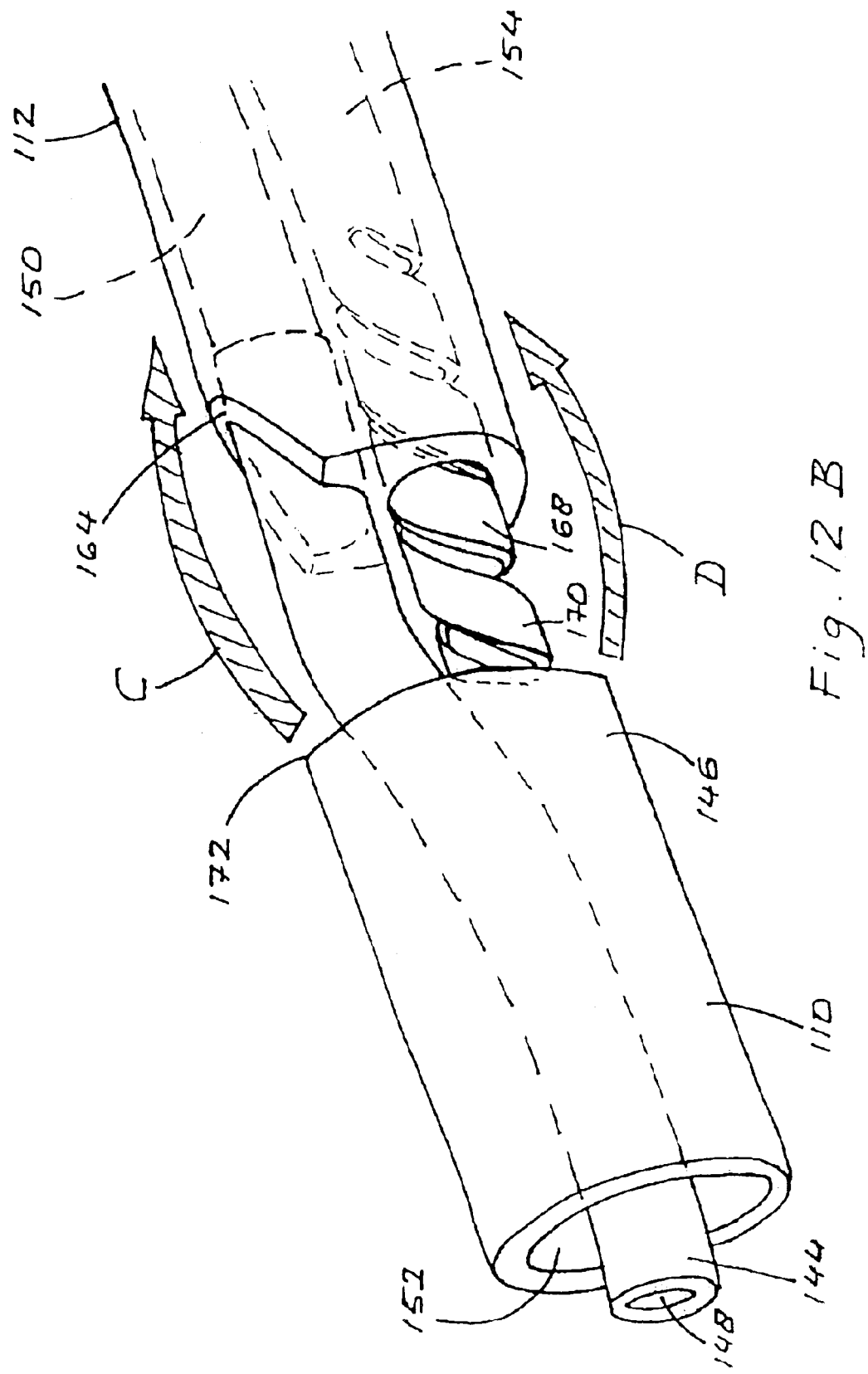
Figure 12E:
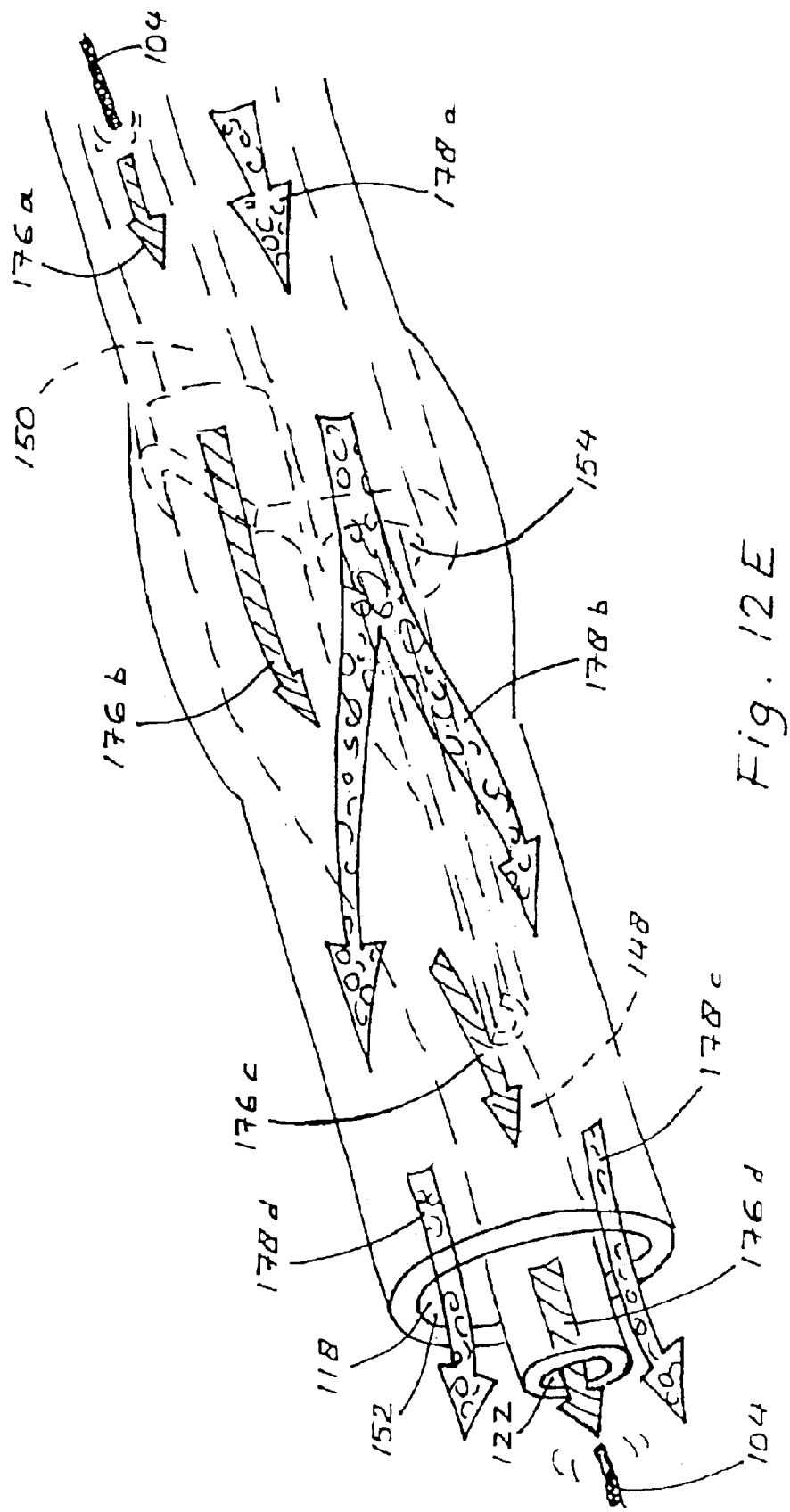

Turning now to FIGS. 9 and 12A–12E, the formation of transition section 114 will be described. As shown, proximal shaft portion 164 adjacent guide wire lumen 150 is cut with an angle to assist in the assembly of catheter 100. Distal shaft inner tube 144 is inserted into proximal shaft guide wire lumen 150 as shown by arrow A. Proximal shaft 112 contains stiffening member 166 that is preferably a hypotube that has a spiral cut section 168 to assist in forming a smooth transition from proximal shaft 112 to distal shaft 110. Hypotube distal section 170 extends from proximal shaft inflation lumen 154 and is inserted into distal shaft inflation lumen 152 as indicated by arrow B. Outer tube proximal end 172 is positioned to overlap proximal shaft distal end 146 as indicated by arrows C and D. The amount of overlap is preferably the minimal such as 3 to 6 mm. Mandrels (not shown) are inserted into guide wire and inflation lumens 148, 150, 152 and 154 to prevent closure of the lumens during application of heat, represented by arrows E-H, to form transition bond 174 as shown in FIG. 12D. While any appropriate heat source may be used, application of laser heat is preferred for a forming a fusion bond that is minimal in size to avoid creating a potential kink point in the catheter while also being fluid tight and able to withstand the necessary pressures in a procedure. Alternatively, other bonding methods may be used such as use of an adhesive. FIG. 12E illustrates the path of guide wire through guide wire lumens 148 and 150 forming overall catheter guide wire lumen 122, designated by arrows 176a–d, and likewise arrows 178a–dc illustrate the pathway of the inflation fluid through lumens 152 and 154 forming overall catheter inflation lumen 118.

Figure 13:
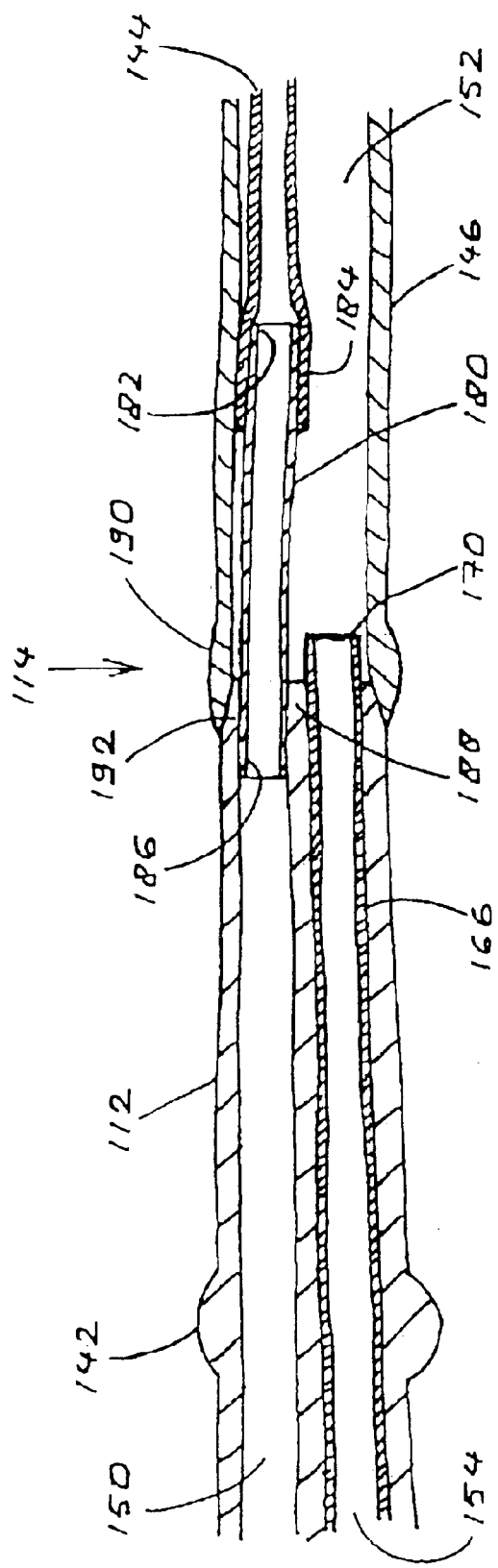
FIG. 13 is a transverse sectional illustration of an alternative embodiment of the transition section of the present invention.
Figure 14:
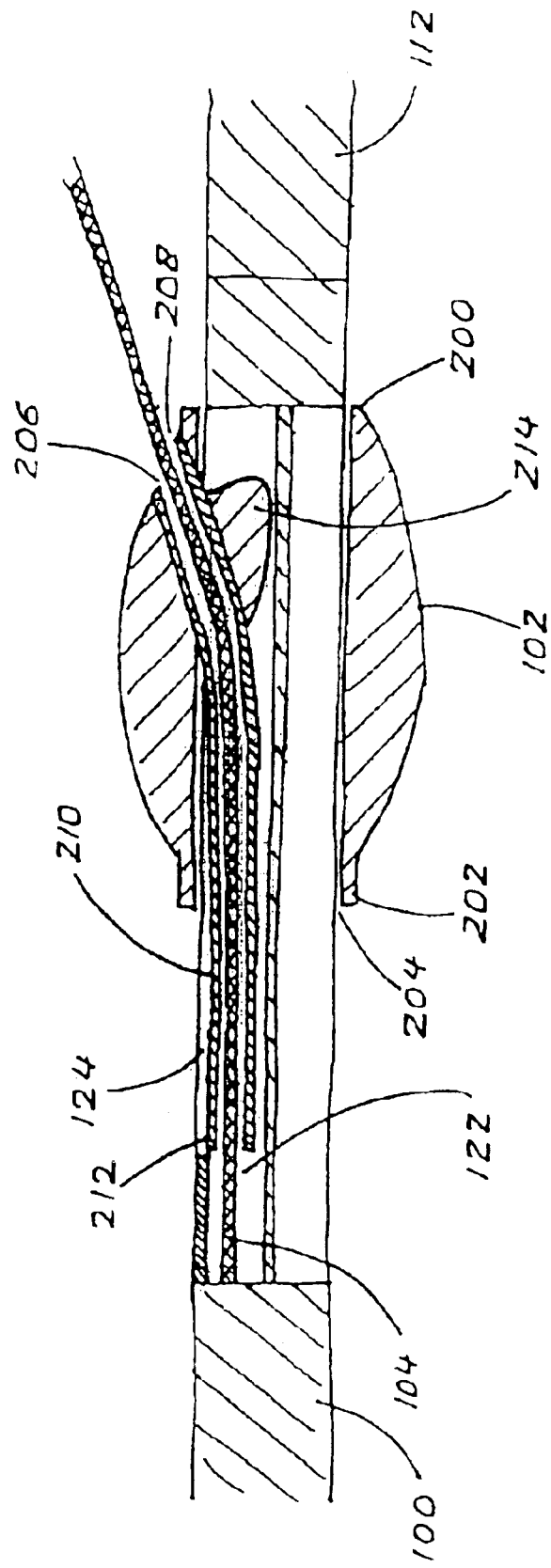
FIG. 14 is a transverse cross-sectional view of the guide member of the present invention.

FIG. 13 shows an alternative embodiment for transition section 114 that incorporates a connecting tube 180. In this embodiment, proximal shaft 112 may be formed from a commonly used catheter material, such as polyethylene. Distal shaft outer tube 146 may likewise be formed from a polyethylene or multilayer extrusion that has an inner layer that readily fuses with the material of proximal shaft 112. Inner tube 144 distal shaft 110 may be made from a commonly used catheter multilayer extrusion having a nylon or polyamide block copolymer outer layer, a polyethylene inner layer and an intermediate tie layer. The nylon or polyamide block copolymer outer layer of inner tube 144 will not readily bond to the polyethylene of proximal shaft 112. Connecting tube 180 is preferably made of polyethylene and is used to assist in bonding tube 144 with the surface of inflation lumen 150 to form a fluid tight seal necessary for the integrity of overall catheter inflation lumen 118. Distal end 182 is inserted into proximal end 184 of inner tube 144 and the tubes are bonded or fused together to form a fluid tight seal. Proximal end 186 is inserted into distal end 188 of inflation lumen 150 and proximal end 190 of outer tube 146 is inserted over distal end 192 of proximal shaft 122. The bonding process to form transition section 114 can then proceed as described with respect to FIGS. 12A–12E.

Figure 15:
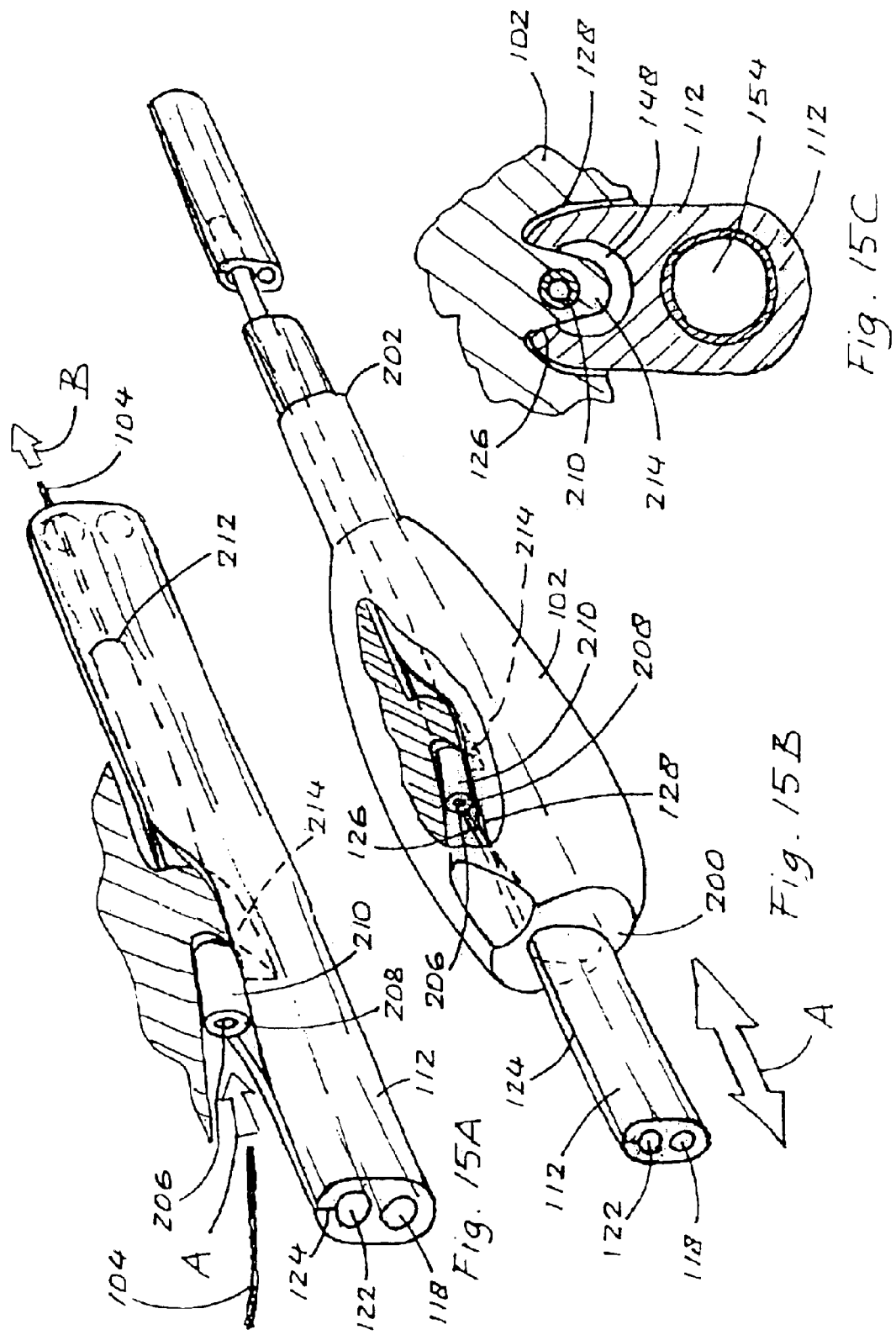
FIGS. 15A–15C show the guide member positioned on the proximal shaft and illustrating the inter-relation between the guide member and the proximal shaft.

Guide member 102 has proximal and distal ends 200 and 202, respectively, as shown in FIGS. 14 and 15A–15C. Catheter passageway 204 extends longitudinally in a generally straight line from guide member proximal end 200 to guide member distal end 202. Guide wire passageway 206 extends from its end 208 through tube 210 into guide wire lumen 122 at its end 212. Guide wire tube 210 is preferably made of polyimide. Catheter proximal shaft 112 extends through catheter passageway 204, engaging keel 214, which extends through guide way 124 in catheter 100 to spread flaps 126 and 128 apart as shown in FIGS. 15A–15C. Guide wire 104 extends through guide wire tube 210 that enters guide wire lumen 122 through spread-apart flaps 126 and 128. During advancement of catheter 100 through guide member 102, flaps 126 and 128 draw together under the influence of the inherent resiliency of the catheter body to close guide way 124, thus enclosing guide wire 102 within guide wire lumen 122. Guide wire 104 is contained within guide wire lumen 122 from guide member 102 to catheter distal end 108. Guide wire 104 may be inserted or removed through guide wire tube 210, while guide member 102 is held stationary with respect to catheter 100 as shown by the arrows A and B in FIG. 15A. In this fashion, guide wire 104 can be exchanged within catheter 100. In yet another type of manipulation, guide member 102 can be held relatively still while catheter 100 is moved through catheter passageway 204, thus bringing guide wire 104 and catheter 100 apart or together, depending on which direction catheter 100 is moved as indicated by arrow A in FIG. 15B.

Figure 16:
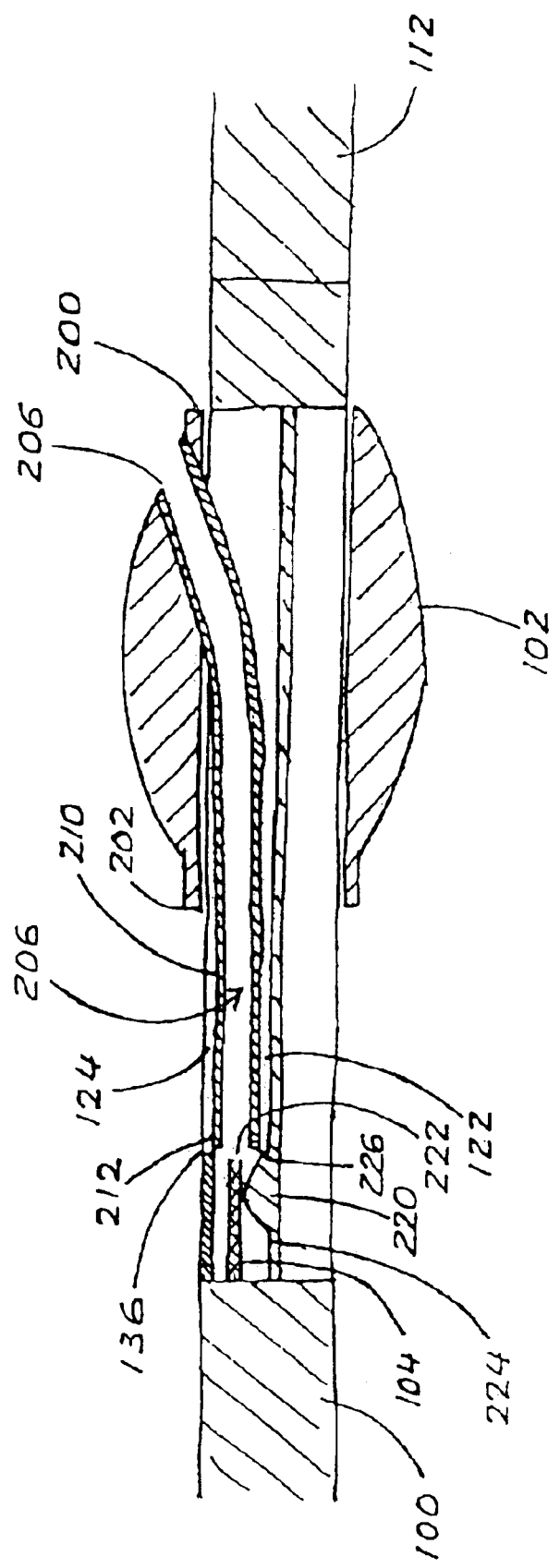
FIG. 16 is an alternative embodiment of the transition section with a ramped guide wire lumen.

In an alternative embodiment shown in FIG. 16, guide wire lumen 122 may include a ramp 220 approximate the distal position of guide wire tube distal end 212. Ramp 220 assists in aligning guide wire 104 into the guide wire passageway 206 as guide wire 104 is back loaded into catheter 100. In a back-loading operation, guide wire 104 is inserted into catheter distal end 108 and threaded proximally through guide wire lumen 122 until guide wire passageway distal end 212 captures the proximal end 222 of guide wire 104 and directs it into guide wire passageway 206. This procedure is typically performed while guide member 102 is positioned adjacent guide way distal end 136. Guide wire passageway distal end 212 may be positioned to be coaxial with guide wire lumen 122. In the guide wire back loading procedure, guide wire 104 may move along lower surface 224 of guide wire lumen 122 and move against lower edge 226 of tube 210 instead of moving into guide wire passageway 206. Ramp 220 acts to assist in aligning guide wire passageway distal end 212 with guide wire proximal end 222 by preventing it from moving against lower edge 226 of tube 210 in order to complete the "back-loading" operation. Ramp 220 may be formed during the extrusion process or by adding the ramp prior to forming the transition section. Alternatively, the ramp may be formed as a part of process for forming the stop or transition section by selecting an appropriate mandrel selected for the guide wire lumen that will permit formation of the ramp.

Figure 17:
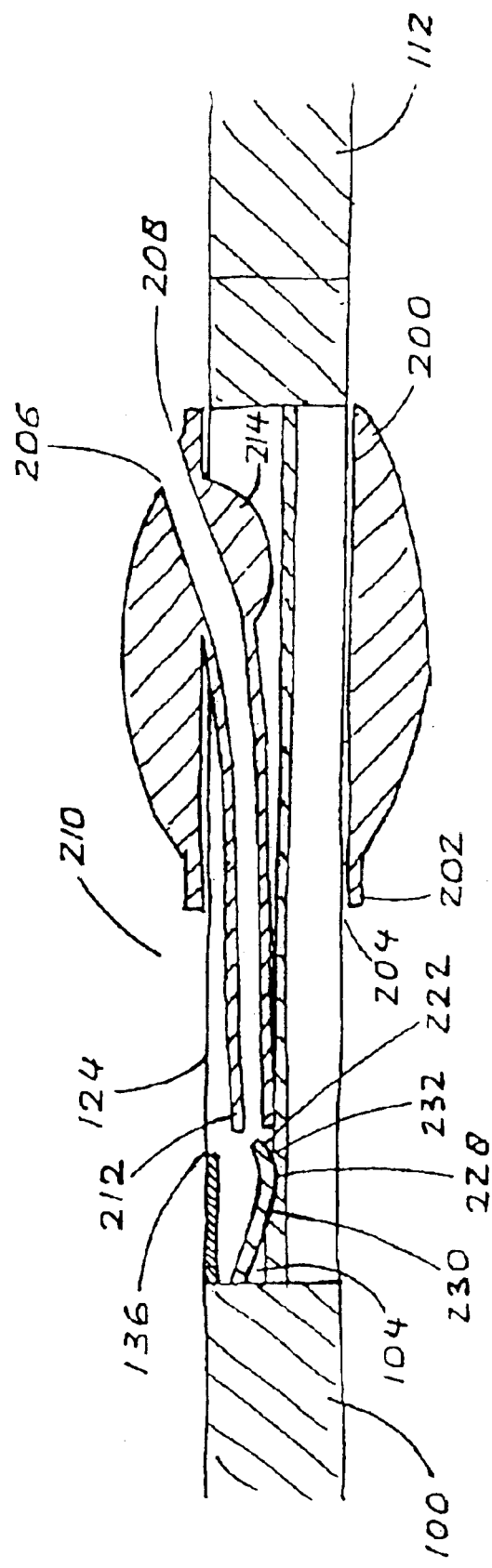
FIG. 17 is a second alternative embodiment of the transition section with a recessed guide wire lumen.

FIG. 17 shows another embodiment of guide wire lumen 122 which includes a recess 228 approximate the distal position of guide wire passage way distal end 212. Recess 228 has distal and proximal sloped surfaces 230 and 232. Recess 228 assists in aligning guide wire 104 with guide wire passageway 206 as guide wire 104 is back loaded into catheter 100. In a back-loading operation, guide wire 104 can be inserted into and threaded proximally through guide wire lumen 122 until guide wire proximal end 222 reaches recess 224. Distal and proximal surfaces 230 and 232 are selected such that if as guide wire proximal end 222 is threaded proximally it is received in recess 228, the sloped surfaces will direct guide wire 104 into guide wire passageway 206 when guide member 102 is positioned adjacent guide way distal end 136. Recess 228 may be formed by removing material prior to the bonding process for the stop or the transition section. Alternatively, an appropriately designed mandrel may be used to form the recess during the heating process for either the formation of the stop or transition section.

While the invention has been particularly shown and described with reference to the preferred embodiments thereof, it will be understood by those skilled in the art that various changes in form and detail may be made there in without departing from the spirit and scope of the invention.

We claim:

1. A catheter and guide wire exchange system comprising:
    an elongate flexible catheter shaft having proximal and distal shafts and first and second lumens extending there through, the first lumen being open at the catheter distal end and being sized and shaped to slidably receive a guide wire;
    a longitudinal guide way formed in the proximal shaft to enable transverse access to the first lumen through the proximal shaft, the guide way extending along a major portion of the length of the proximal shaft from a location adjacent a proximal end of the proximal shaft to a distal terminal end proximal of a distal end of the proximal shaft, thereby defining an uncut distal segment of the proximal shaft;
    a stop located on the proximal shaft at the distal terminal end of the guidewire;
    a balloon mounted about a distal segment of the distal shaft, the balloon being in fluid communication with the second lumen;
    a guide member mounted on the proximal shaft and having a catheter passageway extending there through for slidably receiving the catheter shaft and a guide wire passageway for slidably receiving the guide wire for merging the guide wire and the catheter by guiding the guide wire transversely through the guide way and into the first lumen and for separating the guide wire and catheter by guiding the guide wire transversely out of the first lumen through said guide way; and
    a transition segment between the proximal shaft and the distal shaft, the transition segment comprising the proximal shaft having a cut back section adjacent the first lumen at its distal end and a non cut back section at its distal end, the distal shaft having an outer tube and an inner tube, the distal shaft outer tube abutting the proximal shaft at the cut back section and overlapping the non cut back section of the proximal shaft distal end and the distal shaft inner tube inserted in the first lumen in the proximal shaft.

2. The catheter and guide wire exchange system of claim 1, wherein the guide member has at least one keel disposed within the catheter passageway and being adapted to open and to protrude through the guide way into the first lumen.

3. The catheter and guide wire exchange system of claim 1, wherein the guide wire passageway extends through a tubular member extending into the catheter passageway and being shaped and sized to fit within the first lumen.

4. The catheter and guide wire exchange system of claim 3, wherein the tubular member comprises polyimide tubing.

5. The catheter and guide wire exchange system of claim 1, wherein the first lumen has a ramp adapted to receive and direct a guide wire proximal end through the guide wire passageway.

6. The catheter and guide wire exchange system of claim 1, wherein the first lumen has a recess adapted to receive and direct a guide wire proximal end through the guide wire passageway.

7. The catheter and guide wire exchange system of claim 1 wherein the proximal
    shaft contains a dual lumen arrangement of a side by side tubes defining a guide wire lumen and an inflation lumen and the distal shaft contains a coaxial arrangement of an inner tube defining a guide wire lumen and an outer tube surrounding the inner tube thereby defining an inflation lumen, wherein the transition segment joins proximal and distal shafts intermediate the bilumen and coaxial arrangements.

8. The catheter and guide wire exchange system of claim 1 wherein the outer
    tube of the distal shaft overlaps the proximal shaft distal end and the inner tube of the distal shaft is inserted in the guide wire lumen of the proximal shaft to form the transition section.

9. The catheter and guide wire system of claim 8 wherein the inner tube includes
    a connecting tube segment positioned between the distal shaft inflation lumen and the proximal shaft inflation lumen, the connecting tube segment having a proximal end for insertion into the inflation lumen of the proximal shaft.

10. The catheter and guide wire exchange system of claim 1 wherein the balloon is a stent delivery balloon.

* * * * *